United States Patent
Willner et al.

(10) Patent No.: US 9,809,846 B2
(45) Date of Patent: Nov. 7, 2017

(54) COMPOSITIONS, KITS, USES AND METHODS FOR AMPLIFIED DETECTION OF AN ANALYTE

(71) Applicant: YISSUM RESEARCH DEVELOPMENT COMPANY OF THE HEBREW UNIVERSITY OF JERUSALEM Ltd., Jerusalem (IL)

(72) Inventors: Itamar Willner, Mevasseret Zion (IL); Fuan Wang, Wuhan (CN); Chun-Hua Lu, Fujian (CN); Xiaoqing Liu, Wuhan (CN); Lina Freage, Kfar Kassem (IL)

(73) Assignee: Yissum Research Development Company of The Hebrew University Of Jerusalem Ltd., Jerusalem (IL)

( * ) Notice: Subject to any disclaimer, the term of this patent is extended or adjusted under 35 U.S.C. 154(b) by 253 days.

(21) Appl. No.: 14/586,214

(22) Filed: Dec. 30, 2014

(65) Prior Publication Data
US 2015/0197804 A1    Jul. 16, 2015

Related U.S. Application Data

(60) Provisional application No. 61/922,076, filed on Dec. 30, 2013, provisional application No. 61/923,408, filed on Jan. 3, 2014.

(51) Int. Cl.
*C12Q 1/68* (2006.01)
*C07H 21/04* (2006.01)

(52) U.S. Cl.
CPC ......... *C12Q 1/6844* (2013.01); *C12Q 1/6816* (2013.01)

(58) Field of Classification Search
None
See application file for complete search history.

(56) References Cited

PUBLICATIONS

Wang, Fuan et al "Amplified Detection of DNA through an Autocatalytic and Catabolic DNAzyme-Mediated Process" Angew. Chem., Int. Ed. 50: 295-299 (2011).
Elbaz, Johann et al "Cooperative Multicomponent Self-Assembly of Nucleic Acid Structures for the Activation of DNAzyme Cascades: A Paradigm for DNA Sensors and Aptasensors" Chem.—Eur J. 15: 3411-3418 (2009).
Weizmann, Yossi et al "A Virus Spotlighted by an Autonomous DNA Machine" Angew. Chem., Int. Ed. 45 : 7384-7388 (2006).
Cheglakow, Zoya et al "Diagnosing viruses by the rolling circle amplified synthesis of DNAzymes" Org. Biomol. Chem. 5 : 223-225 (2007).
Zuo Xiaolei et al "Sensitive and Selective Amplified Fluorescence DNA Detection Based on Exonuclease III-Aided Target Recycling" Am. Chem. Soc. 132: 1816-1818 (2010).
Shimron, Simcha et al "Amplified Detection of DNA through the Enzyme-Free Autonomous Assembly of Hemin/G-Quadruplex DNAzyme Nanowires" Anal. Chem. 84:1042-1048 (2012).
Wang, Fuan et al "Autonomous Replication of Nucleic Acids by Polymerization/Nicking Enzyme/DNAzyme Cascades for the Amplified Detection of DNA and the Aptamer-Cocaine Complex" Anal. Chem. 85 : 8196-8203 (2013).
Weizmann, Yossi et al "Autonomous Fueled Mechanical Replication of Nucleic Acid Templates for the Amplified Aptical Detection of DNA" Angew. Chem., Int. Ed. 45 : 2238-2242 (2006).
Patolsky, Fernando et al "Highly Sensitive Amplified Elecronic Detection of DNA by Biocatalyzed Preciptitation of an Insoluble Product onto Electrodes" Chem.—Eur. J. 9 : 1137-1145 (2003).
Wang, Fuan et al "Enzyme-Free Amplified Detection of DNA by an Autonomous Ligation DNAzyme Machinery" Am. Chem. Soc. 134: 5504-5507 (2012).
Lu, Chun-Hua et al "Zn2+-Ligation DNAzyme-Driven Enzymatic and Nonenzymatic Cascades for the Amplified Detection of DNA" Am. Chem. Soc. 134:10651-10658 (2012).
Bi, Sai et al "Triggered Polycatenated DNA Scaffolds for DNA Sensors and Aptasensors by a Combination of Rolling Circle Amplification and DNAzyme Amplification" Anal. Chem. 82 : 9447-9454 (2010).
Bardea, Amos et al "Amplified microgravimetric quartz-crystal-microbalance analyses of oligonucleotide complexes: a route to a Tay-Sachs biosensor device" Chem. Commun. 839-840 (Jan. 1998).

*Primary Examiner* — David Thomas
(74) *Attorney, Agent, or Firm* — Vorys, Sater, Seymour & Pease LLP

(57) ABSTRACT

The invention provides compositions comprising rolling circle amplification sequences and hairpin sequences specifically designed for the accurate and highly sensitive detection of one or more analyte sequences. The invention further provides kits comprising them and methods for their use.

20 Claims, 11 Drawing Sheets
(8 of 11 Drawing Sheet(s) Filed in Color)

COMPOSITIONS, KITS, USES AND METHODS FOR AMPLIFIED DETECTION OF AN ANALYTE

TECHNOLOGICAL FIELD

The invention provides compositions comprising rolling circle amplification sequences, kits comprising them and methods for the accurate and highly sensitive detection of an analyte sequence.

BACKGROUND

The amplified detection of DNA is a continuous challenge in DNA bioanalysis. Different catalysts such as enzymes, catalytic nucleic acids (DNAzymes) or metal nanoparticles (NPs) were used for the amplified detection of DNA. Amplified DNA detection was accomplished by an autocatalytic and catabolic DNAzyme-mediated process. DNA sensing platforms of enhanced sensitivities were designed by the triggering of isothermal autonomous reactions that synthesize numerous DNAzyme units as a result of a single DNA-analyte recognition event. For example, by the design of a circular DNA scaffold, that consists of the replica sequence of the hemin/G-quadruplex, the recognition of the analyte-DNA triggered-on, in the presence of polymerase/dNTPs, the rolling circle amplification (RCA) that generated DNA nanochains of the hemin/G-quadruplex horseradish peroxidase (HRP)-mimicking DNAzyme that enabled the colorimetric or chemiluminescence detection of DNA. Also, by using two functional nucleic-acid-hairpin structures the recognition of the analyte-DNA by one of the DNA hairpins triggered-on the hybridization chain reaction (HCR) that led to DNAzyme chains consisting of the $Mg^{2+}$-dependent DNAzyme or the hemin/G-quadruplex HRP-mimicking DNAzyme. A further approach for amplifying the DNA detection has included, the use of the $Zn^{2+}$-dependent ligation DNAzyme, and the isothermal autonomous synthesis of the ligation DNAzyme units, as a result of the DNA recognition event. Also, DNA machineries consisting of a DNA template, on which the recognition of the target-DNA triggers-on, in the presence of polymerase/dNTPs and a nicking enzyme, the isothermal autonomous synthesis of the hemin/G-quadruplex HRP-mimicking DNAzyme or RNA-cleaving DNAzyme were reported as highly sensitive optical (fluorescent, colorimetric or chemiluminescence) sensing platforms.[9] In contrast to the different amplifying schemes that involve the autonomous synthesis of catalytic labels as a result of the DNA sensing event, an alternative approach that includes the biocatalytic regeneration of the analyte was developed. For example, by using exonuclease III, Exo III, or endonucleases the recognition complexes were cleaved while regenerating the target-analyte for subsequent sensing events. A further goal in DNA sensing involves the multiplexed analysis of several targets. Semiconductor quantum dots (QDs) and micrometer-long metal barcode rods were applied for the multiplexed analysis of DNA using different readout mechanisms such as electrical, fluorescence, Raman spectroscopic fingerprints, fluorescence resonance energy transfer (FRET) and chemiluminescence resonance energy transfer (CRET) processes.

Similarly, the selective desorption of different probes labeled with different fluorophores from graphene oxide supports through the selective formation of probe/analyte duplexes was used for the multiplexed analysis of DNA.

GENERAL DESCRIPTION

In the present application the inventors introduce an amplified, highly-sensitive detection of DNA using the dendritic rolling circle amplification (RCA). The analytical platform includes a circular DNA and a structurally-tailored hairpin structure. The circular nucleic acid template includes a recognition sequence for the analyte DNA, a complementary sequence to a biosensor, and a sequence identical to the loop region of the co-added hairpin structure. The functional hairpin in the system consists of the analyte-sequence that is caged in the stem region and a single-stranded loop domain that communicates with the RCA product. The analyte activates the RCA process, leading to DNA chains consisting of the biosensor and sequences that are complementary to the loop of the functional hairpin structure. Opening of the co-added hairpin releases the caged analyte sequence, resulting in the dendritic RCA-induced synthesis of the biosensor units. The activation of the biosensor using a substrate leads to a fluorescence readout signal. The method enabled the analysis of the target DNA with a very high and sensitive detection limit By the design of two or more different circular DNAs that include recognition sites for two or more different target genes, complementary sequences for two different biosensor sequences, and two different functional hairpin structures, the dendritic RCA-stimulated multiplexed analysis of two or more different genes.

In the present invention the isothermal rolling circle amplification (RCA) process was implemented to trigger a dendritic RCA-induced formation of amplifying DNAzyme catalytic labels. The dendritic RCA-mediated formation of the $Mg^{2+}$-dependent DNAzyme or of the hemin/G-quadruplex HRP-mimicking DNAzyme units and the use of fluorescence, color or chemiluminescence as readout signals for the different sensing platforms was achieved. Furthermore, by applying two different circular DNA templates, the multiplexed analysis of two different genes is demonstrated with the parallel detection of the Tay-Sachs genetic disorder mutant and the gene associated with the TP53 pathogen.

Thus, in the first aspect of the invention there is provides a composition comprising:

at least one hairpin sequence comprising: at least one analyte sequence I'; and at least one sequence II;

at least one circular sequence comprising: at least one sequence I being complementary with sequence I'; at least one sequence II; and at least one sequence III encoding a biosensor sequence III'.

The term "analyte sequence" as used herein should be understood to refer to any nucleotide base sequence that is to be detected in a sample taken from human (or mammalian) subject, non-mammalian animal, parasite, microorganism including bacteria, plant or fungi. The sample may be: a tissue sample, a body fluid sample, a sample from a cell or tissue culture, a sample such as soil, water or food suspected of containing the analyte sequence and the like). Such an analyte sequence may be indicative of a condition, disease or symptom of said human, or the presence of a specific microorganism, bacterial or parasite in a sample (from human, soil, water or food), for the origin of a plant or fungi and the like.

The term "biosensor sequence" refers to any length and type of sequence that is sensitive to triggering by a substrate, which is biologically derived or biomimetic component. Once the biosensor sequence is triggered by a substrate a transducer or the detector element (works in a physico-chemical way; optical, piezoelectric, electrochemical, etc.) that transforms the signal resulting from the interaction of the substrate with the biosensor sequence into another signal (i.e., transduces) that can be more easily measured and optionally also quantified.

The term "circular sequence" refers to a circular molecule of a sequence of nucleotide bases, wherein the 3' and 5' ends of the sequence are connected.

Said at least one circular sequence is triggered into a rolling circle amplification (RCA) process once the analyte sequence I' interacts with its complementary sequence I on said at least one circular sequence. Once this RCA process is triggered said at least one circular sequence produces, with the aid of a polymerase enzyme and a mixture of dNTS, a strand of complementary sequences:
- at least one sequence I produces the complementary sequence I';
- at least one sequence II produces the complementary sequence II'; and
- at least one sequence III produces the biosensor sequence III'.

When en analyte sequence I' is present in a sample it interacts with sequence I of said circular sequence. This interaction triggers the rolling circle amplification (RCA) process producing a complementary sequence of the circular sequence (a repetitive sequence of I'-III'-II'-I'-III'-II' . . . ). Sequence II' of this complementary sequence interacts with sequence II of the hairpin sequence and thus triggers a further the rolling circle amplification (RCA) process for each one. The product is a dendritic sequence that comprises multiple biosensor sequences III'.

It should be understood that sequence II encodes, and is complementary with, sequence II' and is translated to sequence II' once the circular sequence is triggered into the rolling circle amplification (RCA) process. Inherently thereto, sequence II' is complementary to sequence II. This complementarity allows the interaction of sequence II of said at least one hairpin sequence on the strand produced once the RCA process of said at least one circular sequence is triggered.

The terms "complementary" or "complementarity" are used in reference to nucleic acids (i.e. a sequence of nucleotides) related by the well-known base-pairing rules that A pairs with T or U and C pairs with G. For example, the sequence 5'-A-G-T-3' is complementary to the sequence 3-T-C-A-5' in DNA and 3'-U-C-A-5' in RNA. Complementarity can be "partial" in which only some of the nucleotide bases are matched according to the base pairing rules. On the other hand, there may be "complete" or "total" complementarity between the nucleic acid strands when all of the bases are matched according to base-pairing rules. The degree of complementarity between nucleic acid strands has significant effects on the efficiency and strength of hybridization between nucleic acid strands as known well in the art. This is of particular importance in detection methods that depend upon binding between nucleic acids, such as those of the disclosure.

In some embodiments, said biosensor sequence III' is a DNAzyme sequence. In some further embodiments, said DNAzyme is a metal ion dependant DNAzyme. In other embodiments, said DNAzyme is an RNA-cleaving DNAzyme. In some further embodiments, said DNAzyme is hemin/G-quadruplex HRP-mimicking DNAzyme.

In some embodiments of the invention said composition further comprises:
- at least one hairpin sequence comprising: at least one analyte sequence IV'; and at least one sequence V;
- at least one circular sequence comprising: at least one sequence IV being complementary with sequence IV'; at least one sequence V; and at least one sequence VI encoding a biosensor sequence VI'.

In another embodiment of the invention, said analyte sequence I' or IV' is a sensor for at least one disease or disorder.

In other embodiments, said composition of the invention further comprises at least one polymerase enzyme (DNA or RNA polymerase that are suitable for the composition of the invention). In further embodiments, said composition of the invention further comprising dNTPs mixture (a solution containing sodium salts of dATP, dCTP, dGTP and dTTP).

In other embodiments, said composition of the invention further comprises at least one transducer substrate capable of providing a detectable signal from said biosensor sequence. In other embodiments, said transducer substrate is selected from a fluorescence inducing substrate, an optical inducing substrate, a electrochemical inducing substrate, a physico-chemical inducing substrate, a piezoelectric inducing substrate and any combinations thereof. In other embodiments said signal is a fluorescent signal, a physicochemical signal, an optical signal, a piezoelectric signal, a electrochemical signal and any combinations thereof.

The invention further provides a method of detecting at least one analyte sequence I' comprising the steps of:
- Contacting a sample with a composition comprising at least one hairpin sequence comprising at least one analyte sequence I'; and at least one sequence II; and at least one circular sequence comprising: at least one sequence I being complementary with sequence I'; at least one sequence II; and at least one sequence III encoding a biosensor sequence III'; thereby forming a mixture of said sample and composition;
- Detecting the biosensor sequence III' in said mixture;
- thereby detecting said sequence I'.

As used herein the term "detecting", "detection" or "diagnosis" interchangeably used herein, refer to qualitative and optionally quantitative recognition of the existence of analyte sequence in a sample diagnosed. The detection of the analyte sequence is achieved once the dendritic sequence is formed (triggered by the first initial complementary interaction of said analyte sequence with the circular sequence and the formation of the dendritic sequence using the interaction with the hairpin sequence. This dendritic sequence comprises multiple, i.e. at least two, biosensor sequences). The detection of the biosensor sequences using the appropriate substrate (in the transducer component) and readout of the signal provided by the interaction of said biosensor and substrate will give the detection and diagnosis of said analyte sequence in the sample. The detection of said analyte sequence is indicative of a condition, disease or symptom in the subject from which said sample was taken from, and is therefore able to provide information to a professional (such as for example a health care taker) of the condition of said subject, including in some cases the progression of a condition of said subject. In some other embodiments the detection is of an analyte biological sequence in a sample indicating the species or the existence of a biological interaction with the sample (for example in forensic detection, detection of contamination of a subject or sample and so forth). Thus, detection or diagnosis may refer to any type of detection including medical, biological, agricultural, forensic and so forth.

As used herein, the term "sample" is any material obtained from a subject to be analyzed. In some embodiments the sample may be any of a tissue sample, a body fluid sample, a sample from a cell or tissue culture, a sample such as soil, water or food suspected of containing the analyte sequence and the like). In some embodiments the sample is whole blood, sputum, serum, plasma, saliva, cerebrospinal fluid, hair, skin, tissue, or urine. In some other embodiments said sample is not a biological sample, but rather a sample taken from any organic or inorganic object (for example soil, water, liquid, paint, polymer and so forth) wherein a biological analyte sequence can be detected therein.

In some embodiments of a method of the invention said detection is performed by contacting said mixture with a composition comprising at least one transducer substrate capable of providing a detectable signal from said biosensor sequence III'.

The term "transducer substrate" refers to any single or mixture of compounds that are capable of providing a detectable signal from a biosensor sequence of the dendritic sequence produced by the composition of the invention. For example, in embodiments wherein the biosensor is a DNAzyme the binding to a matching oligonucleotide substrate, a detectable (for example fluorogenic) element is cleaved free. The amount of fluorescence can then be measured to tell whether or not a reaction took place.

In the case that an analyte sequence in a sample is attached to the complementary sequence in said circular sequence by a complementary interaction of the bases, this triggers, through the interaction with the hairpin sequence, the formation of a dendritic sequence having multiple biosensor sequences, thus allowing the amplified, accurate and sensitive detection of said analyte sequence in a sample. In other embodiments, said detection is achieved for a concentration of $1*10^{-18}$M or lower of said analyte sequence I' in said sample.

In another aspect the invention provides a method of detecting at least one analyte sequence I' and/or at least one analyte sequence IV' (parallel multiplex detection of different analytes) comprising the steps of:

Contacting a sample with a composition comprising at least one hairpin sequence comprising at least one analyte sequence I'; and at least one sequence II; at least one further hairpin sequence comprising: at least one analyte sequence IV'; and at least one sequence V; at least one circular sequence comprising: at least one sequence I being complementary with sequence I'; at least one sequence II; and at least one sequence III encoding a biosensor sequence III'; and at least one further circular sequence comprising: at least one sequence IV being complementary with sequence IV'; at least one sequence V; and at least one sequence VI encoding a biosensor sequence VI'; thereby forming a mixture of said sample and composition;

Detecting the biosensor sequence III' and/or biosensor sequence VI' in said mixture;

thereby detecting said sequence I' and/or sequence IV'.

The invention further provides a kit comprising at least one component comprising a composition of the invention as disclosed herein above and below and at least one component (either separate or in combination with the other components of the kit) comprising a composition comprising at least one polymeraze enzyme and dNTPs mixture and instructions for use in the detection of an analyte sequence. In further embodiments said kit further comprises a transducer component (either separate or in combination with the other components of the kit) comprising substrate capable of providing a detectable signal from said biosensor sequence. In other embodiments, said transducer substrate is selected from a fluorescence inducing at least one substrate compatible with at least one biosensor sequence capable of inducing a detectable signal. Said substrate may be selected from an optical inducing substrate, a electrochemical inducing substrate, a physicochemical inducing substrate, a piezoelectric inducing substrate and any combinations thereof. In other embodiments said signal is a fluorescent signal, a physicochemical signal, an optical signal, a piezoelectric signal, a electrochemical signal and any combinations thereof.

BRIEF DESCRIPTION OF THE DRAWINGS

The patent or application file contains at least one drawing executed in color. Copies of this patent or patent application publication with color drawings will be provided by the Office upon request and payment of the necessary fee.

In order to better understand the subject matter that is disclosed herein and to exemplify how it may be carried out in practice, embodiments will now be described, by way of non-limiting example only, with reference to the accompanying drawings, in which:

FIG. 3(A) shows the schematic analysis of the target (1) by the RCA-stimulated synthesis of DNA chain consisting of the Mg-dependent DNAzyme units. The fluorescence generated by the DNAzyme-fragmented substrate provides the readout signal for the sensing process. FIG. 3(B) shows the time-dependent fluorescence changes at $\lambda_{em}$=605 nm upon analyzing different concentrations of the target according to the scheme shown in (A): (a) 0, (b) $1\times10^{-12}$, (c) $1\times10^{-11}$, (d) $1\times10^{-10}$, (e) $1\times10^{-9}$, (f) $1\times10^{-8}$, and (g) $1\times10^{-7}$ M. FIG. 3(C) shows the fluorescence spectra generated by the system upon analyzing different concentration of the target (1) for a fixed time-interval of 3 h. (a) to (g) concentrations as in (B). Inset: Derived calibration curve corresponding to the fluorescence intensities at $\lambda_{em}$=605 nm upon analyzing different concentrations of the target (1).

FIG. 4(A) shows the schematic analysis of the target (1) by the dendritic RCA-stimulated synthesis of DNA chains and the amplified generation of the $Mg^{2+}$-dependent DNAzyme units. The fluorescence generated by the DNAzyme-fragmented substrate provides the readout signal for the sensing process. FIG. 4(B) shows the time-dependent fluorescence changes at $\lambda_{em}$=605 nm upon analyzing different concentrations of the analyte (1) according to the scheme shown in FIG. 4(A): (a) 0, (b) $1\times10^{-18}$, (c) $1\times10^{-17}$, (d) $1\times10^{-16}$, (e) $1\times10^{-15}$, (f) $1\times10^{-14}$, (g) $1\times10^{-13}$, (h) $1\times10^{-12}$, (i) $1\times10^{-11}$, (j) $1\times10^{-10}$, (k) $1\times10^{-9}$, (l) $1\times10^{-8}$ and (m) $1\times10^{-7}$ M. FIG. 4(C) shows the fluorescence spectra generated by the system upon analyzing different concentration of the target (1) for a fixed time-interval of 3 h. (a) to (g) concentrations as in (B). Inset: Derived calibration curve corresponding to the fluorescence intensities at $\lambda_{em}$=605 nm upon analyzing different concentrations of the target (1).

FIG. 5(A) shows the schematic analysis of the target (5) by the RCA-stimulated synthesis of DNA chains that trigger the opening of hairpin (8) and the dendritic generation of the $Mg^{2+}$-dependent DNAzyme (domain VIP) units. The fluorescence generated by the DNAzyme-fragmented substrate provides the readout signal for the sensing process. FIG. 5(B) shows the time-dependent fluorescence changes at $\lambda_{em}$=520 nm upon analyzing different concentrations of the target (5) according to the scheme shown in (A): (a) 0, (b) $1\times10^{-18}$, (c) $1\times10^{-17}$, (d) $1\times10^{-16}$, (e) $1\times10^{-15}$, (f) $1\times10^{-14}$, (g) $1\times10^{-13}$, (h) $1\times10^{-12}$, (i) $1\times10^{-11}$, (j) $1\times10^{-10}$, (k) $1\times10^{-9}$, (l) $1\times10^{-8}$ and (m) $1\times10^{-7}$ M. FIG. 5(C) shows the fluorescence spectra generated by the system outlined in FIG. 5(A) upon analyzing different concentration of the target (5) for a fixed time interval of 3 h. (a) to (g) concentrations as in FIG. 5(B). Inset in FIG. 5(C) shows the derived calibration curve corresponding to the fluorescence intensities of FAM at $\lambda_{em}$=520 nm upon analyzing different concentrations of the target (5).

FIG. 6(A) shows the schematic analysis of the target DNA (5) by the RCA-stimulated synthesis of DNA chains consisting of the $Mg^{2+}$-dependent DNAzyme units. The fluorescence generated by the DNAzyme-fragmented substrate provides the readout signal for the sensing process. FIG. 6(B) shows the time-dependent fluorescence changes at $\lambda_{em}$, =520 nm upon analyzing different concentrations of the target DNA (5) according to the scheme shown in FIG. 6(A): (a) 0, (b) $1\times10^{-12}$, (c) $1\times10^{-11}$, (d) $1\times10^{-10}$, (e) $1\times10^{-9}$, (f) $1\times10^{-8}$ and (g) $1\times10^{-7}$M. FIG. 6(C) shows the fluorescence spectra generated by the system outlined in (A) upon analyzing different concentration of the target for a fixed time interval of 3 h. (a) to (g) concentrations as in FIG. 6(B). Inset in FIG. 6(C) shows the derived calibration curve corresponding to the fluorescence intensities of FAM at $\lambda_{em}$=520 nm upon analyzing different concentrations of the target DNA (5).

FIG. 7(A) no target; FIG. 7(B) target (1) only; FIG. 7(C) target (5) only; FIG. 7(D) targets (1) and (5). Curves (a) and (b) correspond to the fluorescence intensities of ROX (at $\lambda_{em}$=605 nm) and FAM (at $\lambda_{em}$=520 nm), respectively.

FIG. 8(A) no target; FIG. 8(B) target (1) only 10 nM; FIG. 8(C) target (5) only, 10 nM; FIG. 8(D) targets (1) and (5), 10 nM each. Curves (a) and (b) correspond to the fluorescence of ROX ($F_1$) and FAM ($F_2$), respectively.

FIG. 9(A) shows the schematic analysis of the target (1) by the RCA-stimulated synthesis of DNA chains that trigger the opening of hairpin (4) and the dendritic synthesis chains consisting of the hemin/G-quadruplex HRP-mimicking DNAzyme units. The DNAzyme catalyzes the $H_2O_2$-mediated oxidation of $ABTS^{2-}$ to colored product $ABTS^{-1}$ or the $H_2O_2$-mediated oxidation of luminol to yield chemiluminescence. FIG. 9(B) shows the time-dependent absorbance changes, following $ABTS^{-1}$ at $\lambda$=420 nm, upon analyzing different concentrations of the target (1), using the sensing platform shown in (A): (a) 0, (b) $1\times10^{18-}$, (c) $1\times10^{17-}$, (d) $1\times10^{16-}$, (e) $1\times10^{15-}$, (f) $1\times10^{14-}$, (g) $1\times10^{13-}$, (h) $1\times10^{12-}$, (i) $1\times10^{-11}$, (j) $1\times10^{10-}$, (k) $1\times10^{9-}$, (l) $1\times10^{8-}$, (m) $1\times10^{7-}$ M, and (n) hemin only. Inset: Calibration curve corresponding to the absorbance changes observed after a fixed time-interval of 3 h upon analyzing different concentrations of the target (1). FIG. 9(C) shows the chemiluminescence spectra corresponding to the analysis of different concentrations of the target (1) according to the scheme outlined in (A). (a) to (n) concentrations as in FIG. 9(B). Inset in FIG. 9(B) and FIG. 9(C) show the calibration curve corresponding to the chemiluminescence intensities at $\lambda$=420 nm upon analyzing different concentrations of the target DNA (1). The dendritic RCA reactions were terminated after a fixed time-interval of 3 h for all the systems.

FIG. 10(A) shows the schematic analysis of the target DNA (1) by the RCA-stimulated synthesis of DNA chains consisting of the hemin/G-quadruplex HRP-mimicking DNAzyme units. The DNAzyme catalyzes the $H_2O_2$-mediated oxidation of $ABTS^{2-}$ to $ABTS^{-1}$ or the $H_2O_2$-mediated oxidation of luminol to yield chemiluminescence. These provide colorimetric or chemiluminescence readout signals for the sensing events. FIG. 10(B) shows the time-dependent absorbance changes, following $ABTS^{-1}$ at $\lambda$=420 nm, upon analyzing different concentrations of the target (1), using the sensing platform shown in (A): (a) 0, (b) $1\times10^{12-}$, (c) $1\times10^{-11}$, (d) $1\times10^{10-}$, (e) $1\times10^{9-}$, (f) $1\times10^{8-}$, (g) $1\times10^{7-}$ M, and (h) hemin only, and (h) hemin only. Inset: Calibration curve corresponding to the absorbance changes observed after a fixed time interval of 5 min upon analysis of different concentrations of the target DNA (1). The RCA reaction was terminated after a fixed time interval of 3 h.

DETAILED DESCRIPTION OF EMBODIMENTS

Experimental Section

Materials: Phi29 DNA polymerase and deoxyribonucleoside 5'-triphosphate mixture (dNTPs), *Escherichia coli* Exonuclease I (Exo I), Exonuclease III (Exo III), T4 polynucleotide kinase, and Quick Ligation™ Kit were obtained from New England BioLabs, Inc. Luminol, and $H_2O_2$ were purchased from Sigma. Hemin was purchased from Frontier Scientific, Inc. A hemin stock solution (1.0 mM) was prepared in DMSO and stored in the dark at −20° C. All DNA oligonucleotides were purchased from Integrated DNA Technologies Inc. (Coralville, Iowa). Table 1 depicts the sequences of the oligonucleotides used in the present invention. The oligonucleotides were HPLC-purified and dissolved in phosphate buffer (10 mM, pH=7.0) to yield stock solutions of 100 μM. Ultrapure water from a NANOpure Diamond (Barnstead) source was used in all of the experiments.

TABLE 1

The DNA sequences used to construct the dendritic RCA circular DNA (sensing systems) of the invention

| SEQ. ID | Sequence |
|---|---|
| SEQ ID 1 | 5' TTA GGA TAG ATA TAC GGG TTC 3' |
| SEQ ID 2 | 5' GG TTA ATC GCT GAA TGAC GAA CCC GTA TAT CTA TCC TAA CAG GAATT AGT AAA CAA TGA AG A TGAC TGTACATGG GTG TAACCT3' |

TABLE 1-continued

The DNA sequences used to construct the dendritic RCA circular DNA (sensing systems) of the invention

| SEQ. ID | Sequence |
| --- | --- |
| SEQ ID 3 | 5' ROX-TGAC TGT TrAG GAA TGAC-Black Hole Quencher-2 3' |
| SEQ ID 4 | 5' GAA CCC GTA TAT CAG GAATT AGT AAA CAA TGA AGA TTA GGA TAG ATA TAC GGG TTC 3' |
| SEQ ID 5 | 5' CCC CTC TGA GTC AGG AAA CAC 3' |
| SEQ ID 6 | 5'GG TTA ATC GCT G AGT ACT GTG TTTCCTGAC TCAGAG GGG CTA ATT ACC ACT AGA CGA TCA TTT TAGG ATA ACA TGG GTG TAA CCT3' |
| SEQ ID 7 | 5' FAM-TAGG ATA TrAG GAG TACT-Black Hole Quencher-1 3' |
| SEQ ID 8 | 5' GTG TTT CCT GACTA ATT ACC ACT AGA CGA TCA TTT CCC CTC TGA GTC AGG AAA CAC 3' |
| SEQ ID 9 | 5' ATC TAT CCT AAC AGG AAT TAG TAA ACA ATG A AGA CCC AAC CCG CCC TAC CCG AAC CCG TAT 3' |
| SEQ ID 10 (L2) | 5' GG TTA ATC GCT GAA TGAC GAA CCC GTA TAT CTA TCC TAA CAG GAATT AGT AAA CAA TGA AGA TGAC TGT ACA TGG GTG TAA CCT 3' |
| SEQ ID 11 (Cap 2) | 5' AGC GAT TAA CC AGG TTA CAC CC 3' |
| SEQ ID 12 (L6) | 5' GG TTA ATC GCT GALT ACT GTG TTT CCT GAC TCA GAG GGG CTA ATT ACC ACT AGA CGA TCA TTT TAGG ATA ACA TGG GTG TAA CCT 3' |
| SEQ ID 13 (Cap 6) | 5' AGC GAT TAA CC AGG TTA CAC CC 3' |
| SEQ ID 14 (L9) | 5' AT CTA TCC TAA CAG GAATT AGT AAA CAA TG A AGA C CCAA CCCG CCCT ACCC GAA CCC GTA T 3' |
| SEQ ID 15 (Cap 9) | 5' TTA GGA TAG ATA TAC GGG TTC 3' |

Figure 1:
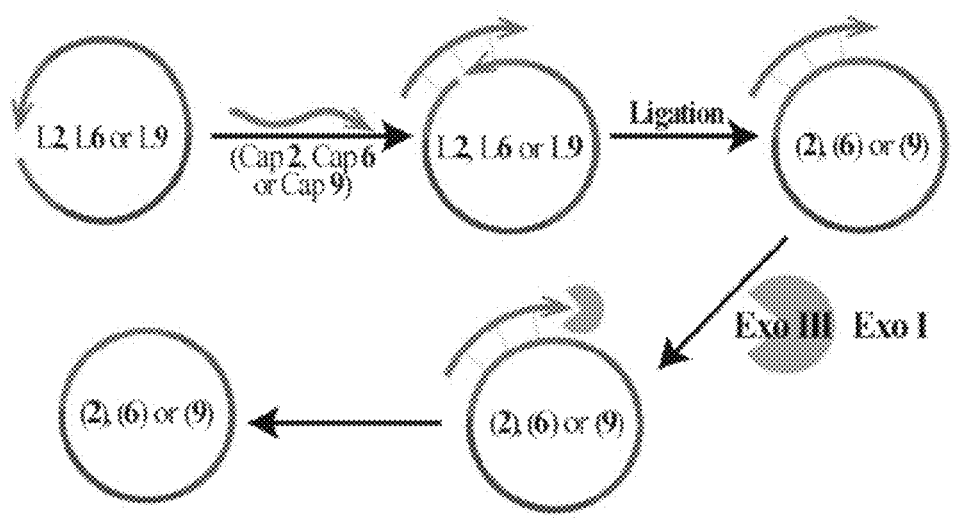
FIG. 1: A schematic synthesis of the circular DNA (2), (6) and (9).
Figure 2:
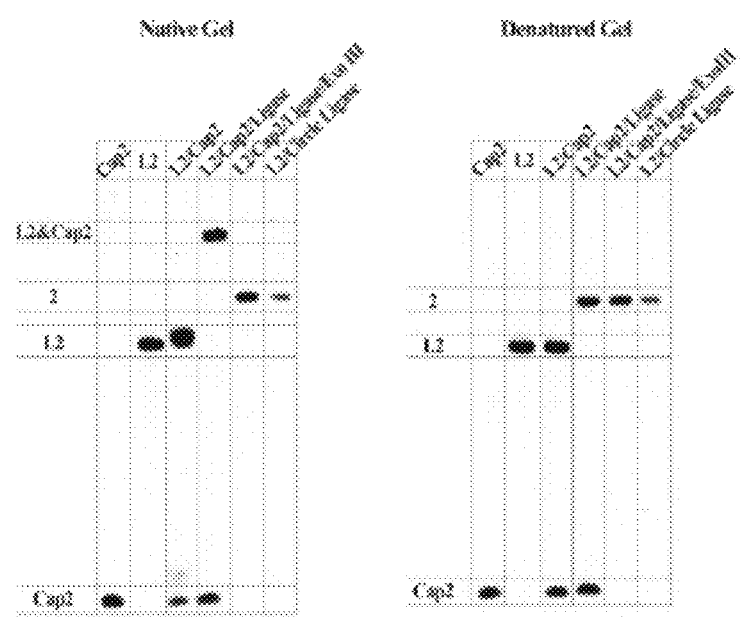
FIG. 2: Gel electrophoresis experiments characterizing the synthesis and the purification of circular DNA (2).

Circular DNA Templates Preparation: The circular DNA templates were prepared as follows (see FIG. 1): First, the linear padlock probe, 10 μM, was phosphorylated using T4 polynucleotide kinase, 0.5 U/μL, in the Quick Ligation™ Kit buffer, at 37° C. for 1 h. Then, the ligation cap primer, 20 μM, and Quick T4 DNA Ligase, 50 U/μL, were introduced into the resulting solution. The ligation reaction was carried out at 20° C. overnight. The enzymes were denatured by heating at 90° C. for 10 mM Subsequently, Exo I (1.0 U/mL) and Exo III (10 U/mL) were added to digest the residual ssDNA and dsDNA for 2 h. The enzymes were denatured by heating at 90° C. for 10 min. The ligated circular DNA product was then purified and separated from the ligation reaction solution using a centrifugal filter devices (Amicon, 3000 MWCO, Millipore Corp.). The as-synthesized circular DNA was stored at 4° C. until use. FIG. 2 exemplifies the gel-electrophoresis results (native gel and denatured gel) corresponding to the synthesis of circular DNA (2) and the respective control entries. Note that we applied a circular ligase to ligate the 3'- and 5'-ends of linear DNA (L2) as a control system for following the synthesis and purification of circular DNA (2) by capping linear DNA (L2) followed by its ligation, according to FIG. 1. FIG. 2 shows the gel electrophoresis experiments characterizing the synthesis and the purification of circular DNA (2).

RCA Assays: In all systems, the fixed concentrations of the hairpin (0.2 μM, for dendritic RCA only), the circular DNA (0.2 μM), the fluorophore/quencher-modified DNAzyme substrate (1.0 μM, for $Mg^{+2}$-dependant DNAzyme only) were employed. Phi29 DNA polymerase (0.5 U/μL), dNTPs (0.2 mM) and different concentrations of the target DNA were included to initiate the RCA reaction. The RCA process was performed in a buffer solution consisting of 50 mM Tris-HCl, pH 7.5, 20 mM $MgCl_2$ and 1 mM DTT. Fluorescence measurements were performed using a Cary Eclipse spectrometer (Varian inc). For the readout of the dendritic RCA synthesis of the hemin/G-quadruplex HRP-mimicking DNAzyme, colorimetric measurements were performed in a solution consisting of the products, hemin (0.1 μM), $H_2O_2$ (44 μM), $ABTS^{2-}$ (0.18 mM) in a 10 mM HEPES buffer solution (pH 7.4, 200 mM NaCl). Absorbance changes were followed at λ=420 nm to characterize the rate of the oxidation of $ABTS^{2-}$ to $ABTS^{-}$ by $H_2O_2$. Chemiluminescence measurements were performed using a photon counting spectrometer (Edinburgh Instruments, FLS 920) equipped with a cooled photomultiplier detection system, connected to a computer (F900 v.6.3 software). Measurements were made in a 10 mM HEPES buffer solution (pH 8.5, 200 mM NaCl), which included the product, hemin (0.1 μM), luminol (0.5 mM) and $H_2O_2$ (30 mM).

Results and Discussion

Figures 3A, 3B, 3C:
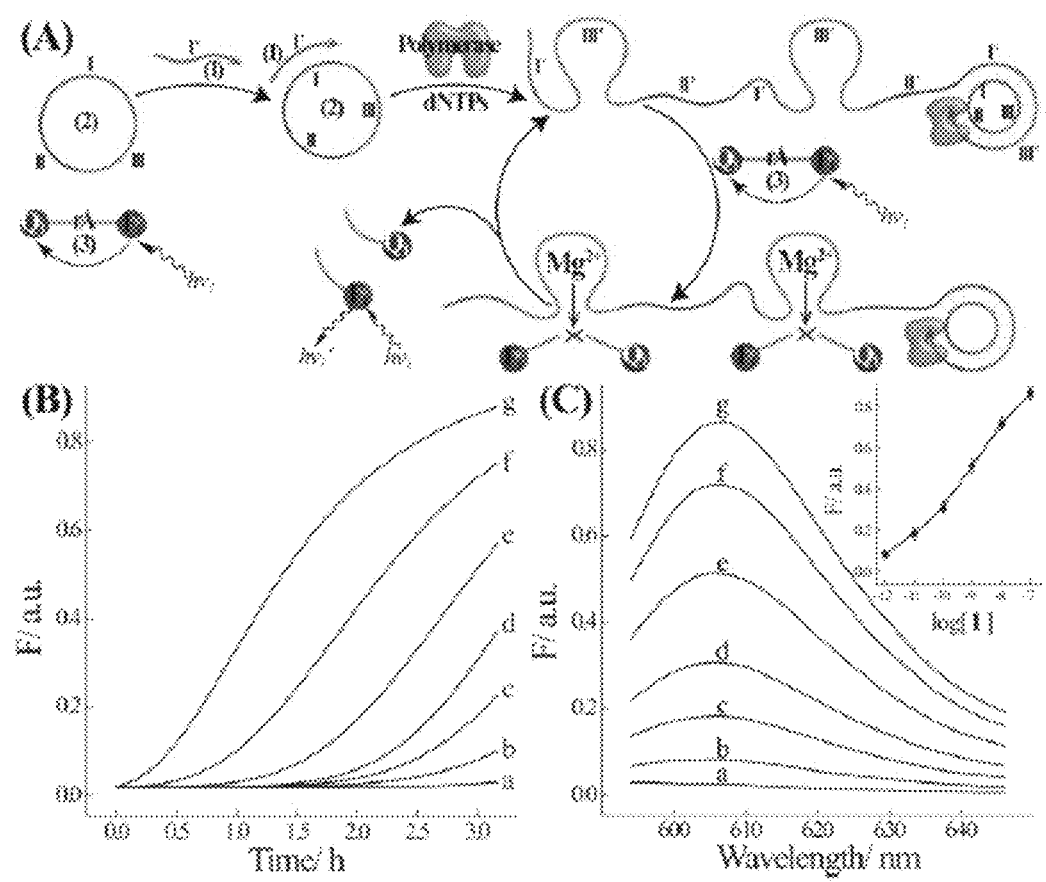
FIG. 3A-3C.

The basic rolling circle amplified (RCA) detection of the analyte-DNA, the Tay-Sachs genetic disorder mutant (1), is depicted schematically in FIG. 3(A). The sensing system includes the circular DNA (2) composed of the domain I (complementary to the analyte sequence I'), the region II, and the sequence III that is complementary to the $Mg^{2+}$-dependent RNA-cleaving DNAzyme sequence. Also, the ribonucleobase (rA)-containing nucleic acid (3), modified by a fluorophore/quencher ($F_1/Q_1$) pair (where $F_1$=6-Carboxyl-X-Rhodamine, ROX; $Q_1$=Black Hole Quencher-2), acts as the substrate of the $Mg^{2+}$-dependent DNAzyme. In the presence of the analyte (1), polymerase and the dNTPs mixture, the RCA process is triggered-on, leading to the isothermal autonomous synthesis of the RCA chains composed of the repeat units I'-III'-II' (where domain III' is composed of the $Mg^{2+}$-dependent DNAzyme sequence). The substrate (3) is modified at its 5'- and 3'-ends with a fluorophore/quencher ($F_1$/Q1) pair, respectively, resulting in the quenching of the luminescence of the fluorophore ($F_1$=ROX, $\lambda_{em}$=605 nm). The formation of the DNAzyme chains triggers the cleavage of the substrate (3), leading to a fluorescence signal, and this provides the readout signal for the analysis of the target-DNA (1). FIG. 3(B) shows the time-dependent fluorescence changes at $\lambda_{em}$, =605 nm upon analyzing different concentrations of the analyte (1) by the system outlined in FIG. 3(A). Non-linear increase in the time-dependent fluorescence changes is observed, consistent with the increase in the content of DNAzyme reporter units as the RCA process proceeds. FIG. 3(C) shows the fluorescence spectra observed upon analyzing different concentrations of the analyte (1) according to FIG. 3(A), and running the RCA amplification process for a fixed time-interval of 3 h. As the concentration of the analyte is higher, the resulting fluorescence is intensified, consistent with the higher content of RCA-generated $Mg^{2+}$-dependent DNAzyme units. FIG. 3(C) inset shows the resulting calibration curve corresponding to the fluorescence intensities of ROX ($F_1$) at $\lambda_{em}$=605 nm upon analyzing different concentrations of the target-DNA (1), implying that the analyte could be analyzed with a detection limit that corresponds to 1 pM.

Figures 4A, 4B, 4C:
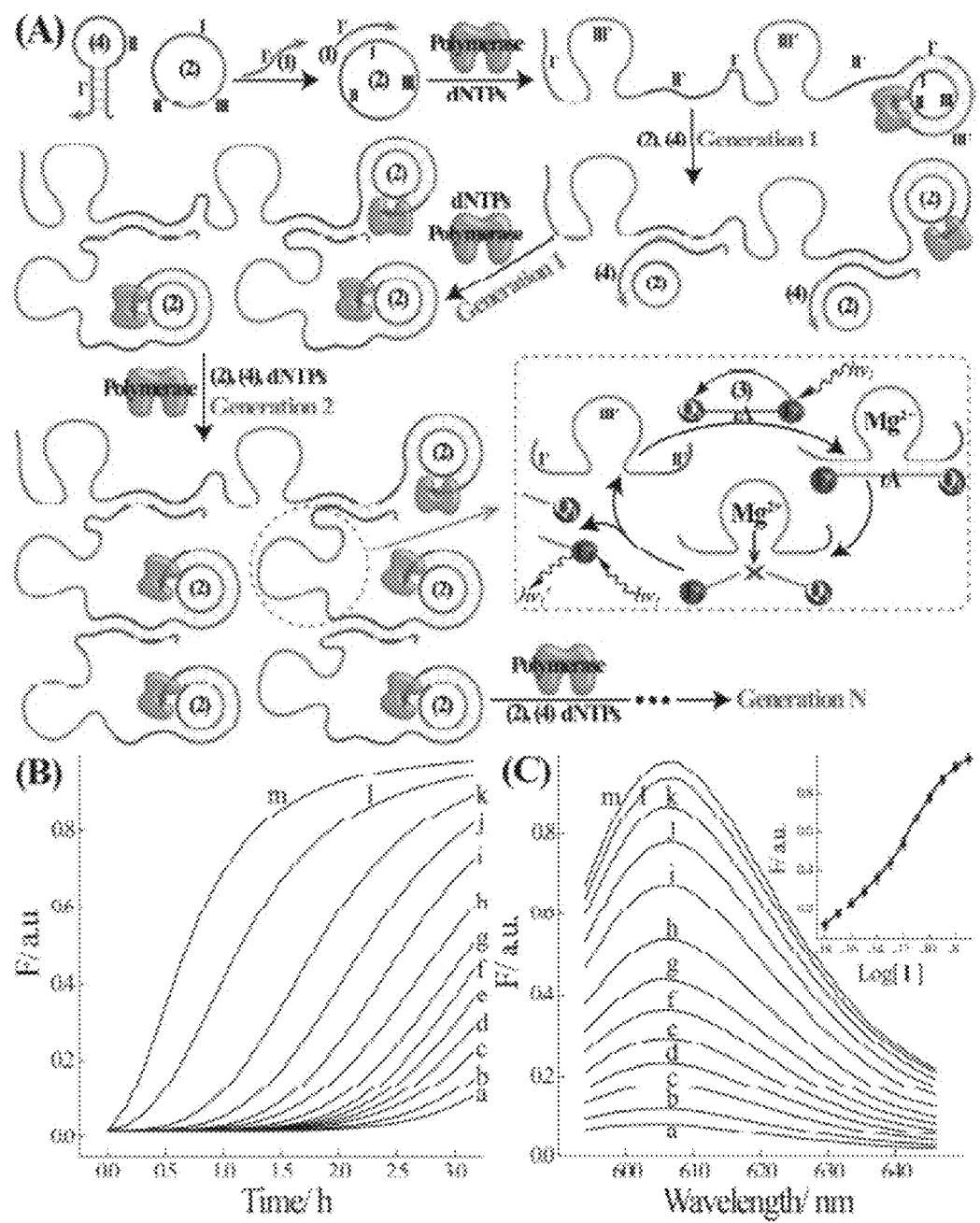
FIG. 4A-4C.

FIG. 4(A) depicts the dendritic RCA detection of the analyte (the Tay-Sachs genetic disorder mutant (1)) using the $Mg^{2+}$-dependent DNAzyme as catalytic reporter, and fluorescence as readout signal. The system consists of the circular DNA (2), that includes three functional sequences (I—the recognition sequence for the analyte, II—the complementary sequence for the dendritic branching element of the RCA reactions, and III—the complementary sequence of the $Mg^{2+}$-dependent DNAzyme), the fluorophore/quencher ($F_1/Q_1$)-functionalized substrate (3) of the DNAzyme, and the hairpin structure (4), acting as key-element for the dendritic RCA reaction. The hairpin structure (4) is composed of a stem region that includes the analyte sequence I' (complementary to the sequence I of circular DNA (2)) and a loop region comprising of the sequence II, present in the circular DNA (2). Under these conditions the sequence I' of the hairpin is blocked in an inactive structure. In the presence of the analyte (1) and the polymerase/dNTPs mixture, the RCA process is triggered-on the circular DNA template (2), leading the RCA chains composed of the I'-III'-II' repeat units. The component II' associated with the nanochains is, however, complementary to the single-stranded loop II associated with the hairpin structure (4). This results in the hybridization of the sequences II' of the RCA chains to the loop region of the hairpin (4), leading to the opening of the hairpin, and the release of the free sequence of the analyte, domain I', that was originally caged in the stem region of the hairpin. The resulting released sequence I' binds to the circular DNA template (2), resulting in the first generation of branched RCA chains comprising of the I'-III'-II' repeat units. That is, the primary recognition of the analyte (1) by the circular template (2) triggers the isothermal autonomous dendritic formation of branched RCA chains consisting of the $Mg^{2+}$-dependent DNAzyme sequences III'. The hybridization of the substrate (3) to the DNAzyme sequences triggers-on the cleavage of the substrate, and the generation of fluorescence ($F_1$=ROX, $\lambda_{em}$=605 nm). FIG. 4(B) shows the time-dependent fluorescence changes at $\lambda_{em}$=605 nm upon analyzing different concentrations of the analyte (1) by the system outlined in FIG. 4(A). A non-linear increase in the fluorescence intensities is observed. Interestingly, the intense fluorescence changes include an induction time-interval after which a sharp increase in the fluorescence is observed. As the concentration of the analyte (1) is lower the induction time interval is longer, and the onset in the fluorescence increase appears after a longer time interval. These results are consistent with the non-linear dendritic RCA formation of the $Mg^{2+}$-dependent DNAzyme units. The lower the concentration of the target (1), the longer the time-interval is needed for the generation of this threshold value. For optimal sensitivity and S/N>3 the target DNA (1) was analyzed after a fixed time-interval of 3 h. This time interval was selected due to the observation that the background fluorescence signal of the system in the absence of the analyte is almost zero for a time-interval of 3 h, and after this time-gap a perturbing sharp increase in the background fluorescence is observed. Note that the system includes in the absence of the target (1) the hairpin structure (4) that includes in its stem region the caged sequence of the target. As traces of the open hairpin are always present in the system, these trace amount of target sequences (I') activate the dendritic RCA process and the autonomous synthesis of the $Mg^{2+}$-dependent DNAzyme reporter units.

Figures 5A, 5B, 5C:
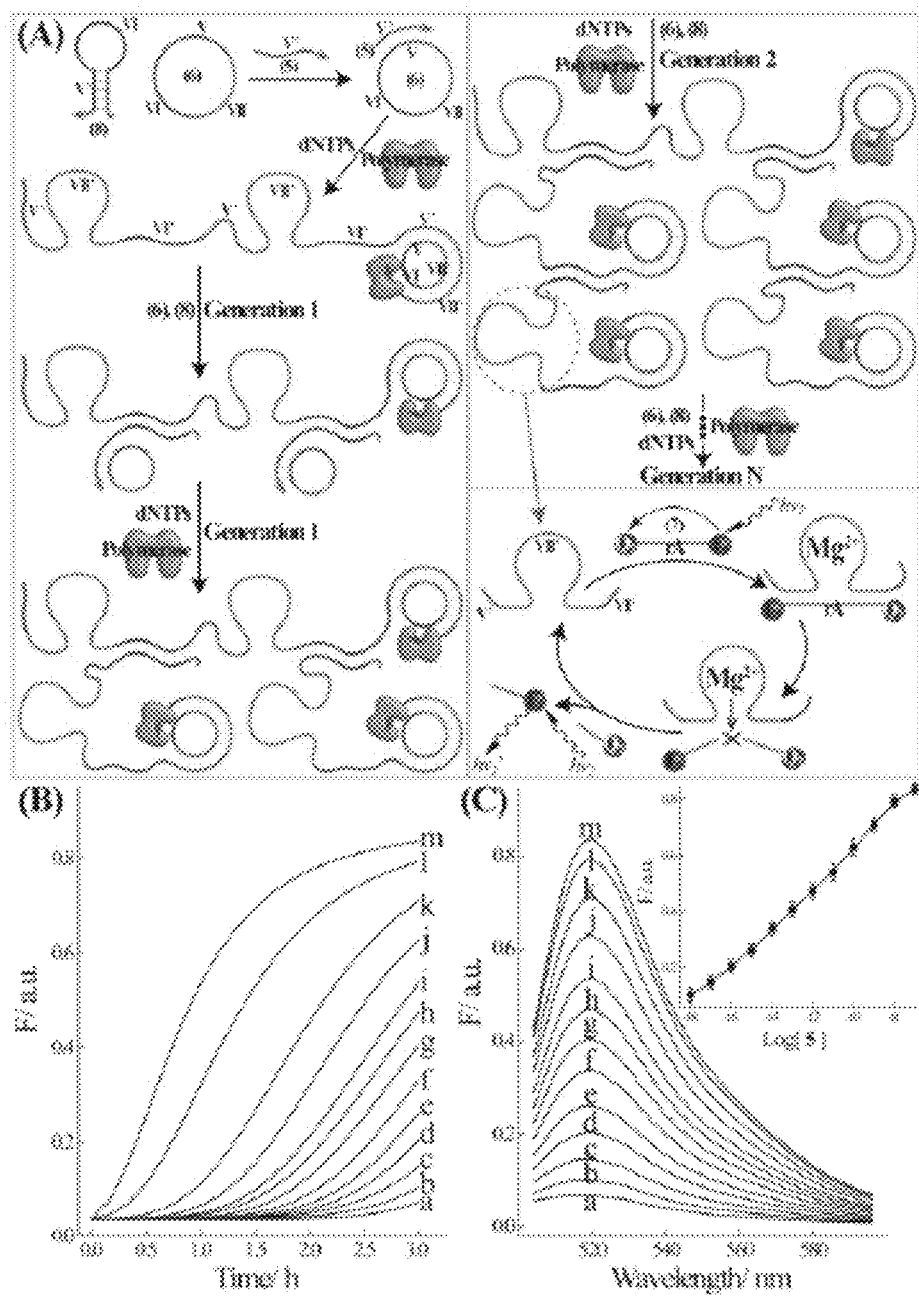
FIG. 5A-5C.
Figures 6A, 6B, 6C:
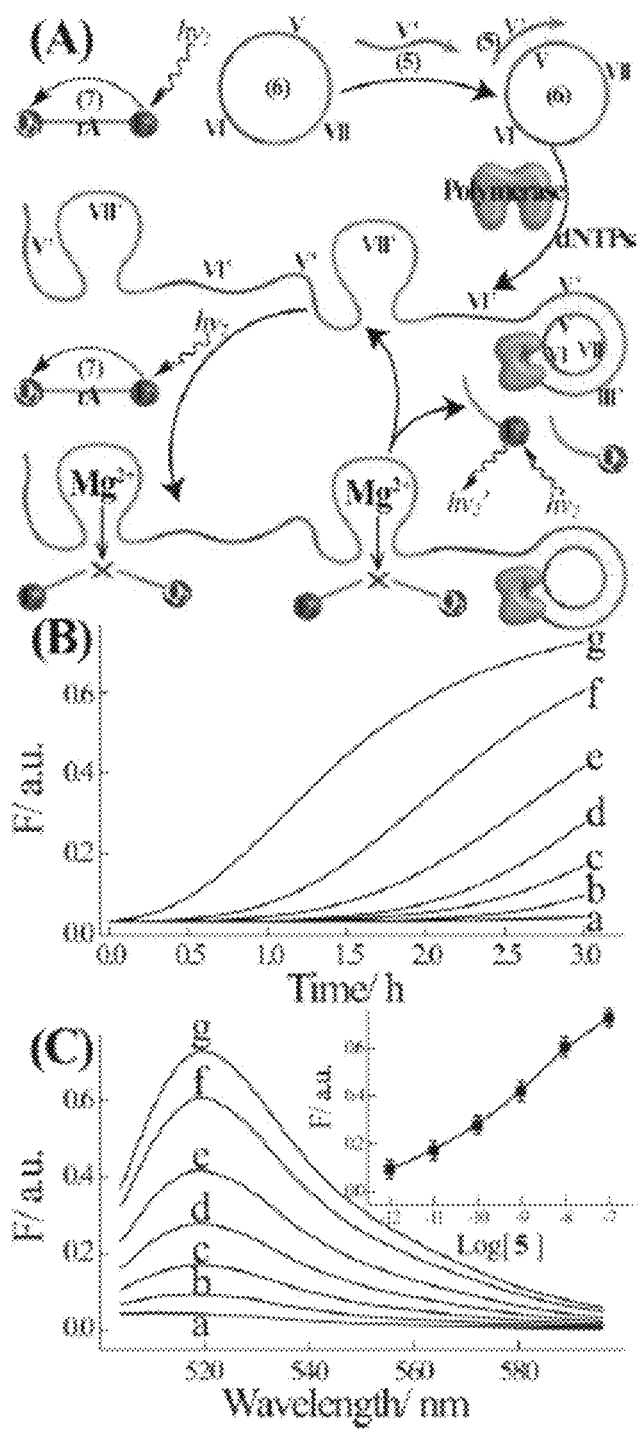
FIG. 6A-6C.

Nonetheless, due to the low concentration of the open hairpins the time-interval required to reach the set-on fluorescence changes is longer than three hours. That is, the analysis of the target DNA by the dendritic RCA machinery is unperturbed for a time-interval of three hours. FIG. 4(C) shows the resulting fluorescence spectra corresponding to the analysis of different concentrations of the target DNA (1) by the system outlined in FIG. 4(A) for a fixed time-interval of 3 h. FIG. 4(C) inset shows the resulting calibration curve corresponding to the fluorescence intensities of ROX at $\lambda_{em}$=605 nm upon analyzing different concentrations of the target DNA (1). The detection limit for analyzing Tay-Sachs genetic disorder mutant (1) by the dendritic RCA synthesis of the $Mg^{2+}$-dependent DNAzyme units is 1 aM. The use of the Mg-dependent DNAzyme as a reporter unit for the sensing event enables the design of multiplexed dendritic RCA amplification schemes. The $Mg^{2+}$-dependent DNAzyme requires a conserved nucleic acid sequence for binding of the $Mg^{2+}$-ion and a conserved base-sequence containing a ribonucleobase (rA) that acts as substrate for the DNAzyme, and hybridizes with the complementary bases associated with the DNAzyme sequence. The tethering of tandem base sequences at the 3'- and 5'-ends of the conserved DNAzyme sequences, and the elongation of the respective 5'- and 3'-ends of the substrates with complementary tandem base sequences allows the tailoring of diverse $Mg^{2+}$-dependent DNAzymes that bind different substrates. Thus, by modifying the different substrates with different fluorophore/quencher units, diverse catalytic DNAzyme labels for multiplexed analyses may be envisaged. That is, by encoding in the base sequence of the circular DNA template the information to synthesize different $Mg^{2+}$-dependent DNAzymes, the multiplexed, parallel analysis of different targets may be achieved. Accordingly, a second circular DNA (6) was designed, and a new functional hairpin structure (8) for the dendritic RCA-stimulated synthesis of the $Mg^{2+}$-dependent DNAzyme nanowires for the amplified detection of a second target, the TP53 gene (5), see FIG. 5. The circular DNA template (6) includes the recognition sequence (domain V) for the target gene (5), the sequence (domain VI) that provides the initiator unit for the dendritic branching mechanism and the domain VII that consists of the sequence complementary to the tailored $Mg^{2+}$-dependent DNAzyme. Also, the hairpin structure (8) and the F2/Q2-labeled substrate (7) (where $F_2$=6-carboxyfluorescein, FAM; Q2=Black Hole Quencher-1) are included in the system. The hairpin structure (8) includes in its single-stranded loop domain the sequence VI and in its stem region the caged target sequence V'. In the presence of the analyte (5) and polymerase/dNTPs mixture the RCA process over the template (6), proceeds to yield the DNA chains composed of the repeat units V'-VII'-VI'. The autonomous opening of the hairpin units (8) by the sequences VI' in the RCA-generated nanochains, and the association of the hairpin-released target domains V' to further circular template (6) units triggers the dendritic formation of branched RCA chains that include the tailored $Mg^{2+}$-dependent DNAzyme sequences for cleaving the substrate (7) and releasing the $F_2$-labeled fragmented nucleic acid ($F_2$=FAM, $\lambda_{em}$=520 nm) as fluorescence readout signal for analyzing the target (5). This enables the amplified detection of the target gene (5) with a detection limit corresponding to 1 aM (For the detailed detection of the target gene (5) by the regular RCA process generating the Me-dependent DNAzyme units and by the dendritic RCA-stimulated synthesis of the $Mg^{2+}$-dependent DNA units, see FIG. 6 and FIG. 7. A mixture consisting of the circular DNA (2) and the hairpin (4) pair was implemented with the circular DNA (6) and the hairpin (8) pair for the multiplexed analysis of the two targets (1) or/and (5) using (3) and (7) as substrates for the $Mg^{2+}$-dependent DNAzymes generated by the respective circular DNA/hairpin pairs. The resulting fluorescence of the fragmented substrates $F_1$ or/and $F_2$ ($F_1$=ROX, $\lambda_{em}$'=605 nm; $F_2$=FAM, $\lambda_{em}$=520 nm) provides then the readout signal for the respective analyte. The multiplexed analysis of the targets (1) or/and (5) is shown in FIG. 8.

Figures 7A, 7B, 7C, 7D:
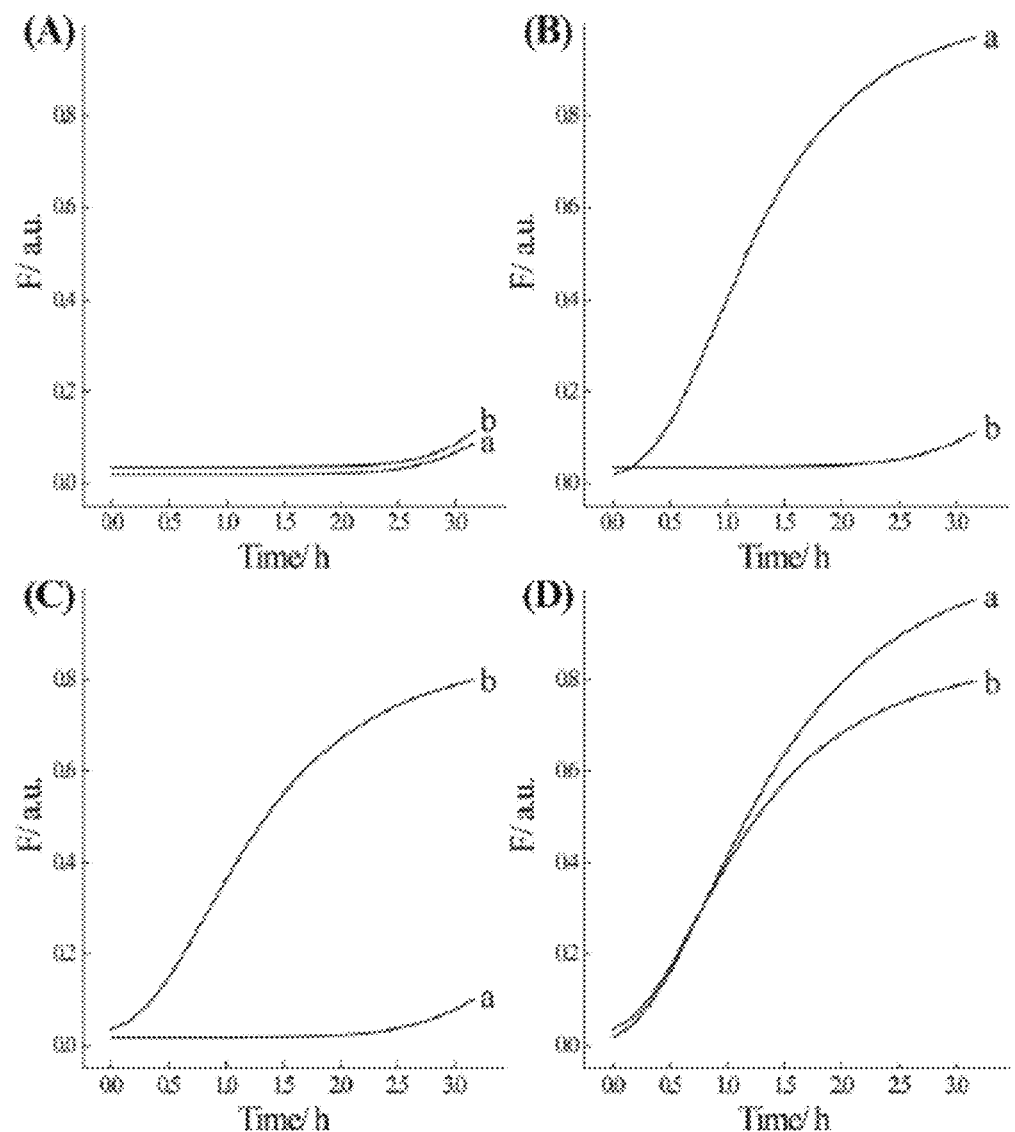
FIG. 7A-7D: shows the time-dependent fluorescence changes upon the multiplexed analysis of the targets (1) and/or (5), each 10 nM, using the amplification scheme shown in FIG. 1(A).
Figures 8A, 8B, 8C, 8D:
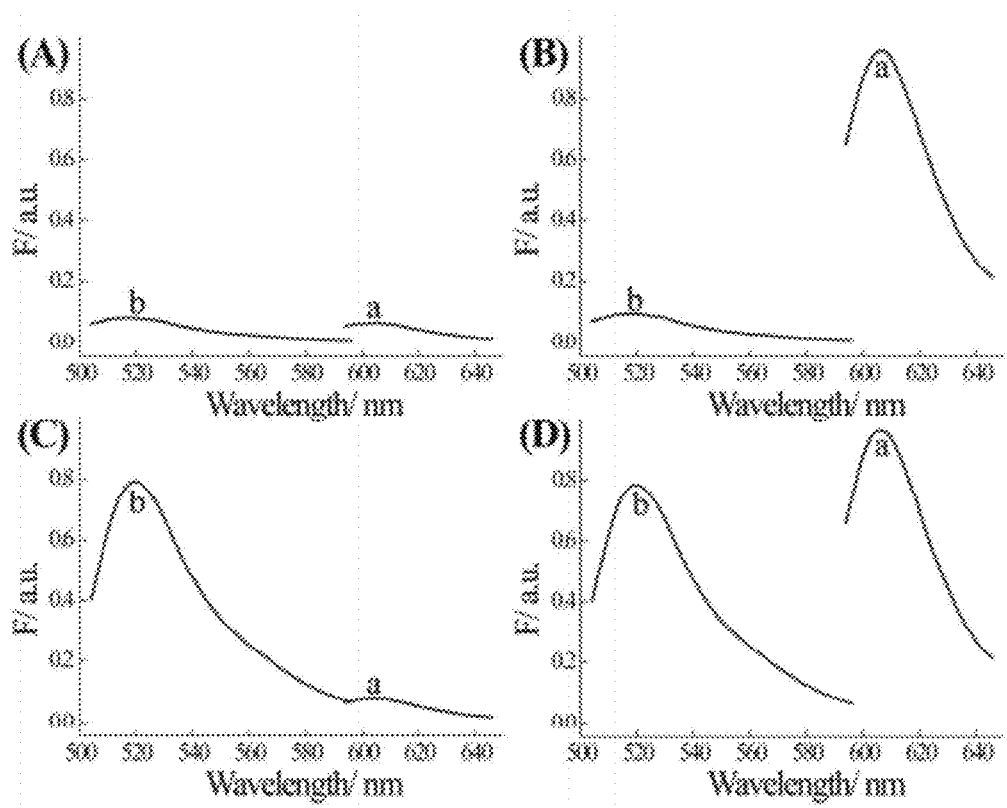
FIG. 8A-8D: shows the flurescence spectra generated by the dendritic RCA system after a fixed time-interval of 3 h upon analyzing.

The analysis of the two targets are presented, 10 nM each, by the dendritic RCA mechanism using the $Mg^{2+}$-dependent DNAzyme-generation of the fluorophore-labeled DNA fragments as readout signals. FIG. 7, shows the time-dependent fluorescence changes upon analyzing each of the targets (1) or/and (5) by the composite mixture. FIG. 8 shows the fluorescence spectra of the system generated after a fixed time-interval of 3 h upon subjecting the analyzing mixture to no target, FIG. 8(A); target (1) only, FIG. 8(B); target (5) only, FIG. 8(C); and upon subjecting the mixture to the two targets (1) and (5) together, FIG. 8(D). The fluorescence of $F_1$ (ROX, $\lambda_{em}$=605 nm) is triggered-on upon analyzing the analyte (1), whereas the fluorescence of $F_2$ (FAM, $X_{em}$=520 nm) is activated in the presence of the analyte (5). In the presence of the two targets the fluorescence of $F_1$ and $F_2$ are activated, and thus, the multiplexed analysis of the two targets is demonstrated.

Figures 9A, 9B, 9C:
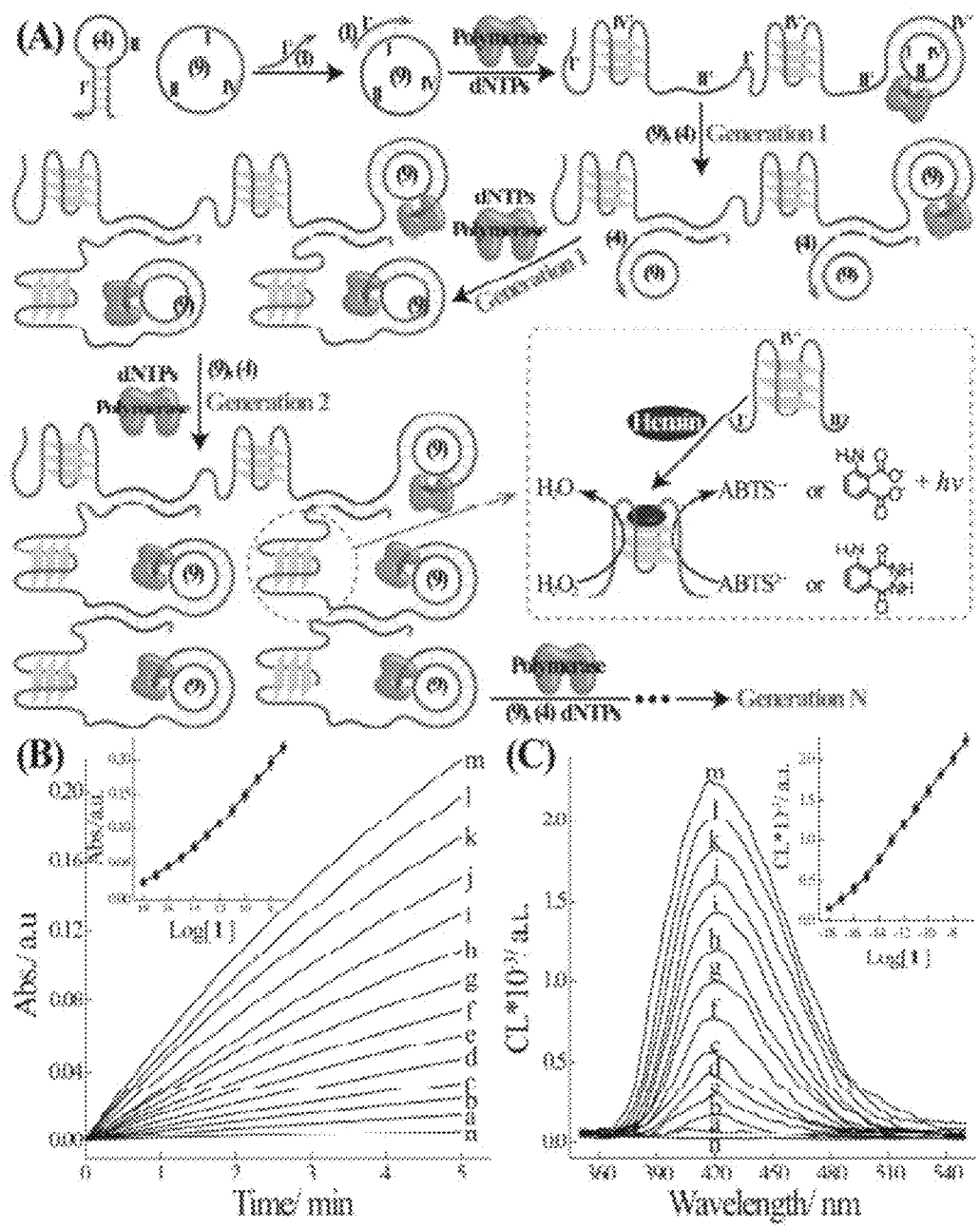
FIG. 9A-9C.

The use of other DNAzymes as catalytic reporter units for the dendritic RCA process enables the implementation of DNAzymes with high turnover numbers and the use of DNAzyme that produce readout signals other than fluorescence. This was demonstrated by the implementation of the hemin/G-quadruplex HRP-mimicking DNAzyme. This DNAzyme allows the catalyzed colorimetric or chemiluminescence transduction of the sensing events. Accordingly, the dendritic RCA detection of target (1) was achieved by applying the hemin/G-quadruplex HRP-readout signals via the DNAzyme-catalyzed oxidation of 2,2'-azino-bis-(3-ethylbenzothialine)-6-sulfonic acid ($ABTS^{2-}$) to colored product $ABTS^{-1}$ by $H_2O_2$ or the DNAzyme-catalyzed oxidation of luminol by $H_2O_2$, respectively. The system included a circular DNA (9) as template, and the hairpin structure (4) as functional unit that triggers the dendritic RCA process, FIG. 9(A). The circular DNA (9) is composed of the sequence I that is complementary to the target (1), the sequence II provides the branching element for the dendritic RCA, and the domain IV consists of the sequence complementary to the hemin/G-quadruplex DNAzyme. In the presence of the analyte (1) and the polymerase/dNTPs mixture, the RCA process is initiated to yield the RCA chain consisting of the repeat units I'-IV'-II'. The component II' in the RCA chains opens hairpin (4), leading to the release of the free analyte sequence I'. The uncaging of the analyte sequence and its hybridization with the circular template units (9), results in the dendritic branching of the RCA process and the amplified detection of the target (1). The dendritic RCA-generated chains include the domain IV' corresponding to the G-quadruplex sequence. As a result, the branched hemin/G-quadruplex DNAzyme units are formed, and these catalyze the formation of the color or chemiluminescence as readout signals. FIG. 9(B) depicts the time-dependent absorbance changes as a result of the hemin/G-quadruplex DNAzyme-catalyzed oxidation of $ABTS^{2-}$ by $H_2O_2$ to yield colored product $ABTS^{-1}$ ($?_{max}$=420 nm) according to the system outlined in FIG. 9(A). As the concentration of the analyte (1) increases the absorbance changes are higher. FIG. 9(B) inset depicts the calibration curve corresponding to the absorbance changes generated by the dendritic RCA detection system after a fixed time-interval of 3 h upon analyzing different concentrations of the target DNA (1). The detection limit for analyzing the target DNA (1) by the RCA-stimulated dendritic synthesis of the hemin/G-quadruplex DNAzyme and the colorimetric detection, corresponds to 1 aM (For the detailed detection of the target gene (1) by the regular RCA process generating the hemin/G-quadruplex DNAzyme units, see FIG. 10). Similarly, FIG. 9(C) shows the chemiluminescence spectra generated by the hemin/G-quadruplex DNAzyme formed by the dendritic RCA process outlined in FIG. 9(A) for a fixed time-interval of 3 h and through the DNAzyme-catalyzed oxidation of luminol by $H_2O_2$. FIG. 9(C) inset shows the resulting calibration curve relating the chemiluminescence intensity at $\lambda$=420 nm generated by the dendritic RCA detection system, in the presence of variable concentration of the target (1). The resulting detection limit is comparable to the detection limit observed in the colorimetric detection system, 1 aM. The disadvantage of the system consisting of the dendritic RCA synthesis of the hemin/G-quadruplex HRP-mimicking DNAzyme is, however, the fact that multiplexed analyses of targets is difficult. For the comparison of the present amplification sensing platform to other isothermal DNA amplification systems, see Table 2. For a comparison corresponding to the specific sensing of the Tay-Sachs gene by the present sensing platform and other reported systems, see Table 3. The information included in Tables 2 and Table 3 indicates that the present method reveals superior analytical performance for analyzing DNA, and specifically for the detection of the Tay-Sachs gene.

TABLE 2

A comparison of the sensitivities observed upon analyzing DNA genes by different isothermal amplification machineries

| Amplification Machinery | Sensing duration | Detection Limit | Readout signal | Ref. |
|---|---|---|---|---|
| Catabolic regeneration of the target by using $Mg^{2+}$-dependent DNAzyme as amplifying label | 12 h | $1 \times 10^{-12}$ M | Fluorescence | 1 |
| A $Mg^{2+}$-dependent DNAzyme/horseradish peroxidase (HRP)-mimicking hemin/G-quadruplex DNAzyme amplifying cascade | 7 h | $1 \times 10^{-12}$ M | Color | 2 |
| Polymerase/Nicking enzyme/HR P-mimicking DNAzyme machinery | 1.5 h | $1 \times 10^{-14}$ M | Color & Chemiluminescence | 3 |
| Polymerase-stimulated rolling circle amplified (RCA) synthesis of the HRP-mimicking DNAzyme | 2 h | $1 \times 10^{-14}$ M | Color & Chemiluminescence | 4 |
| Exonuclease III regeneration of the analyte | 24 h | $1 \times 10^{-17}$ M | Fluorescence | 5 |
| Hybridization chain reaction synthesis of the HRP-mimicking DNAzyme wires | 4-6 h | $1 \times 10^{-13}$ M | Color & Chemiluminescence | 6 |
| Polymerase/Nicking enzyme induced regeneration of the target while synthesizing the $Mg^{2+}$-dependent DNAzyme as ampamplifying label | 4-6 h | $1 \times 10^{-18}$ M | Fluorescence | 7 |
| Dendritic RCA synthesis of the $Mg^{2+}$-dependent DNAzyme or the HRP-mimicking DNAzyme | 3 h | $1 \times 10^{-18}$ M | Fluorescence, Color & Chemiluminescence | The present invention |

TABLE 3

Analyzing the Tay-sachs gene by different amplification schemes

| Amplification Machinery | Sensing duration | Detection Limit | Readout signal | Ref. |
|---|---|---|---|---|
| Autonomous fueled replication of a template by using Folk 1 endonuclease | 2 h | $1 \times 10^{-14}$ M (Buffer) | Fluorescence | 8 |
| Biocatalytic precipitation of an insoluble product on electrode | 0.5 h | $5 \times 10^{-14}$ M (Buffer) $5 \times 10^{-13}$ M (Buffer) | Faradaic impedance Sepecscopy | 9 |
| An autonomous ligation DNAzyme machinery | 2 h | $1 \times 10^{-11}$ M (Buffer) | Fluorescence | 10 |
| $Zn^{2+}$-ligation DNAzyme machinery | 4-5 h | $1 \times 10^{-11}$ M (Buffer) | Fluorescence | 11 |
| Rolling circle amplified synthesis of the HRP-mimicking DNAzyme | 1.5 h | $1 \times 10^{-16}$ M (Buffer) | Chemiluminescence | 12 |
| Amplified microgravimetric detection using antibodies | 4-6 h | $6 \times 10^{-8}$ M (Buffer) | Microgravimetric quartz-crystal-microbalance | 13 |
| Dendritic RCA synthesis of the $Mg^{2+}$-dependent DNAzyme or the HRP-mimicking DNAzyme | 3 h | $1 \times 10^{-18}$ M (Buffer) $5 \times 10^{-15}$ M (Buffer) | Fluorescence& Color | Present invention |

REFERENCES (1) Wang, F.; Elbaz, J.; Teller, C.; Willner, I. *Angew. Chem., Int. Ed.* 2011, 50, 295-299.
(2) Elbaz, J.; Moshe, M.; Shlyahovsky, B.; Willner, I. *Chem.-Eur. J.* 2009, 15, 3411-3418.
(3) Weizmann, Y.; Beissenhirtz, M. K.; Cheglakov, Z.; Nowarski, R.; Kotler, M.; Willner, I. *Angew. Chem., Int. Ed.* 2006, 45, 7384-7388.
(4) Cheglakov, Z.; Weizmann, Y.; Basnar, B.; Willner, I. *Org. Biomol. Chem.* 2007, 5, 223225.
(5) Zuo, X.; Xia, F.; Xiao, Y.; Plaxco, K. W. *J. Am. Chem. Soc.* 2010, 132, 1816-1818.
(6) Shimron, S.; Wang, F.; Orbach, R.; Willner, I. *Anal. Chem.* 2012, 84, 1042-1048.
(7) Wang, F.; Freage, L.; Orbach, R.; Willner, I. *Anal. Chem.* 2013, 85, 8196-8203.
(8) Weizmann, Y.; Cheglakov, Z.; Pavlov, V.; Willner, I. *Angew. Chem., Int. Ed.* 2006, 45, 2238-2242.
(9) Patolsky, F.; Lichtenstein, A.; Willner, I. *Chem.-Eur. J.* 2003, 9, 1137-1145.
(10) Wang, F.; Elbaz, J.; Willner, I. *J. Am. Chem. Soc.* 2012, 134, 5504-5507.
(11) Lu, C. H.; Wang, F.; Willner, I. *J. Am. Chem. Soc.* 2012, 134, 10651-10658.
(12) Bi, S.; Li, L.; Zhang, S. *Anal. Chem.* 2010, 82, 9447-9454.
(13) Bardea, A.; Dagan, A.; Ben-Dov, I.; Amit, B.; Willner, I. *Chem. Commun.* 1998, 839-840

Figures 10A, 10B:
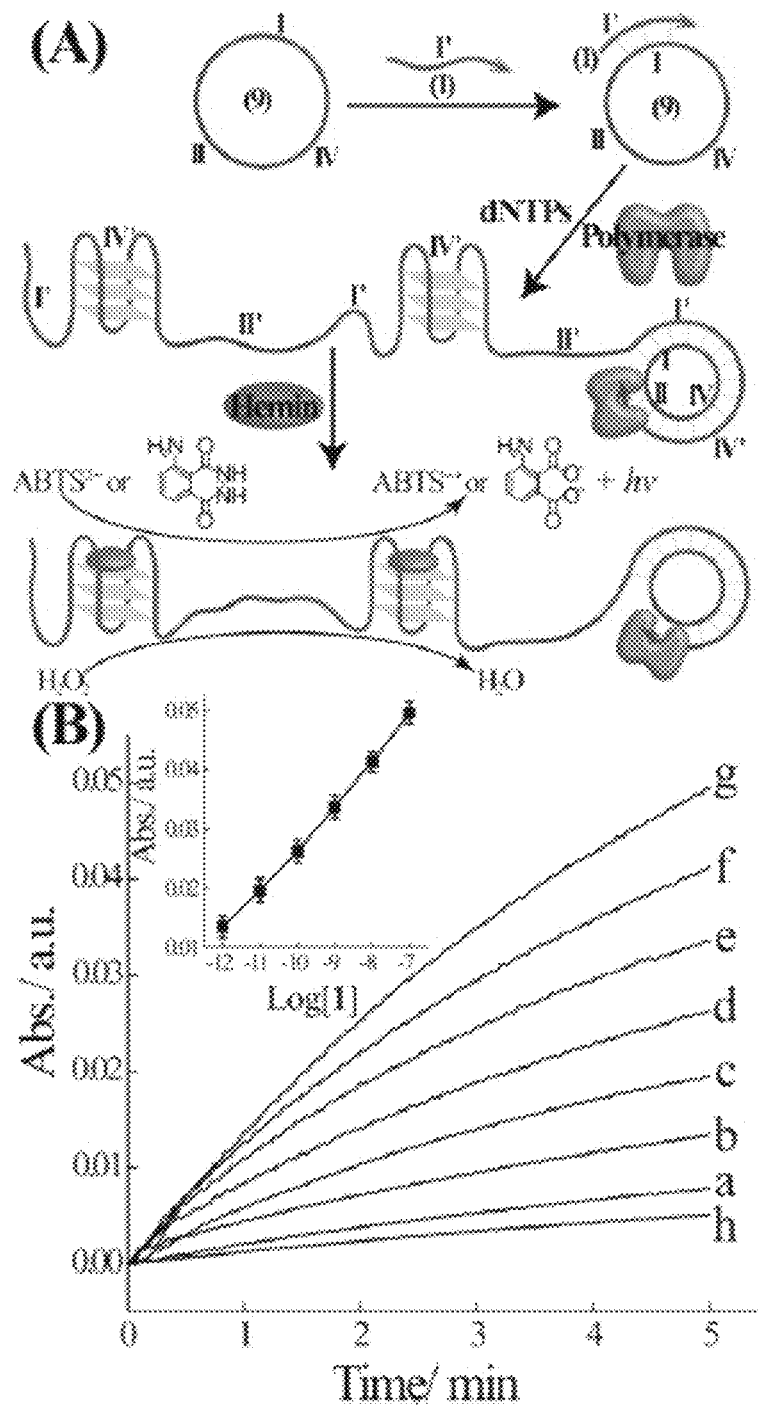
FIG. 10A-10B.

In order to examine the implementation of the amplified sensing platform of DNA in "real" bioenvironments, the detection of the target-DNA (1) in plasma samples was examined using the dendritic RCA process that leads to the formation of the hemin/G-quadruplex DNAzyme according to FIG. 9(A). Toward this end, variable concentrations of the target (1) were dissolved in plasma, the samples were diluted to 5%, and subjected to the dendritic RCA analyses using the hemin/G-quadruplex DNAzyme-catalyzed oxidation of $ABTS^{2-}$ to colored product $ABTS^{-1}$ by $H_2O_2$ as readout signal. FIG. 10(A) shows the schematic analysis of the target DNA (1) by the RCA-stimulated synthesis of DNA chains consisting of the hemin/G-quadruplex HRP-mimicking DNAzyme units. The DNAzyme catalyzes the $H_2O_2$-mediated oxidation of $ABTS^{2-}$ to $ABTS^{-1}$ or the $H_2O_2$-mediated oxidation of luminol to yield chemiluminescence. These provide colorimetric or chemiluminescence readout signals for the sensing events. FIG. 10(B) shows the time-dependent absorbance changes, following $ABTS^{-1}$ at λ=420 nm, upon analyzing different concentrations of the target (1), using the sensing platform shown in (A): (a) 0, (b) $1\times10^{12-}$, (c)

Figure 11:
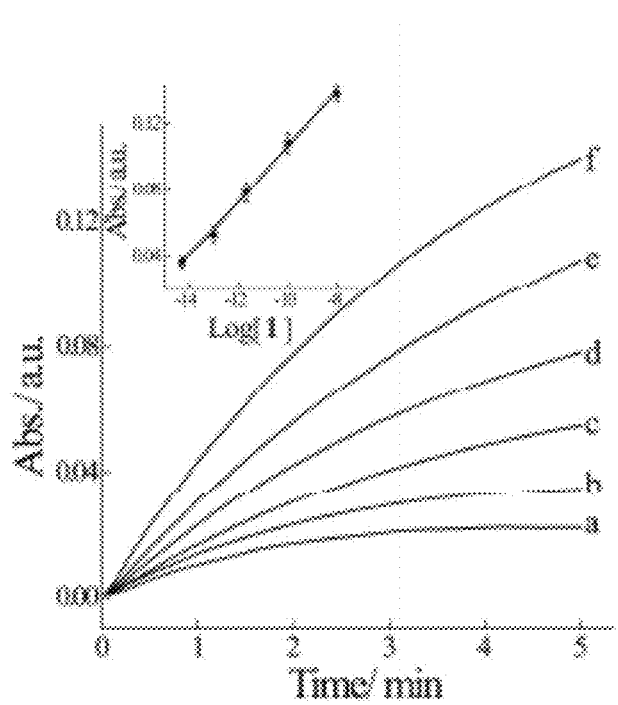
FIG. 11: shows the time-dependent absorbance changes, following $ABTS^{-1}$ at $\lambda$=420 nm, upon analyzing different concentrations of the target (1) in plasma, using the sensing platform shown in FIG. 9(A): (a) 0, (b) $5\times10^{15-}$, (c) $1\times10^{-13}$, (d) $2\times10^{12-}$, (e) $1\times10^{10-}$ and (f) $1\times10^{8-}$ M. Inset: Calibration curve corresponding to the absorbance changes observed after a fixed time-interval of 3 h upon analyzing different concentrations of the target (1).

$1\times10^{-11}$, (d) $1\times10^{10-}$, (e) $1\times10^{9-}$, (f) $1\times10^{8-}$, (g) $1\times10^{7-}$ M, and (h) hemin only, and (h) hemin only. The RCA reaction was terminated after a fixed time interval of 3 h. FIG. 11 shows the time-dependent absorbance changes of ABTS upon analyzing different concentrations of (1) in the plasma. The results imply that the target (1) could be sensed with a detection limit of 5.0 fM in the plasma samples, with a reproducibility of ±5% (N=5 experiments).

The present invention has extended the isothermal rolling circle amplification (RCA) process to a RCA-stimulated dendritic synthesis of catalytic nucleic acids (DNAzymes) sensing platform. The method is based on the improvement of the RCA sensing methods by two elements: (i) The introduction of a functional hairpin that regenerates the analyte and allows the dendritic branching of the RCA chains. (ii) The isothermal autonomous formation of DNAzymes in the RCA chains. These catalytic labels enabled the fluorescent, colorimetric or chemiluminescent detection of the analytes. By the tailoring of different circular DNA templates that lead to the formation of different RCA-branched DNAzyme reporter catalysts, the multiplexed analysis of different analytes was demonstrated. The isothermal autonomous RCA-stimulated dendritic generation of DNAzymes enabled the ultrasensitive detection of the analyte.

The invention claimed is:

1. A composition comprising:
   at least one hairpin selected from the group consisting of SEQ. ID. NO. 4 and SEQ. ID. NO. 8, the at least one hairpin sequence comprising
      at least one analyte sequence I', and
      at least one sequence II; and
   at least one circular sequence selected from the group consisting of SEQ. ID. NO. 2, SEQ. ID. NO. 6 and SEQ. ID. NO. 9, the at least one circular sequence comprising
      at least one sequence I being complementary with sequence I',
      at least one sequence II, and
      at least one sequence III encoding a biosensor sequence III'.

2. The composition according to claim 1, wherein said biosensor sequence III' is a DNAzyme sequence.

3. The composition of claim 1, wherein said bio sensor sequence III' is a DNAzyme sequence of a metal ion dependant DNAzyme.

4. The composition of claim 1, wherein said biosensor sequence III' is a DNAzyme sequence of an RNA-cleaving DNAzyme.

5. The composition of claim 1, wherein said biosensor sequence III' is a DNAzyme sequence of a hemin/G-quadruplex HRP-mimicking DNAzyme.

6. The composition according to claim 1, further comprising:
   at least one additional hairpin sequence comprising
      at least one analyte sequence IV', and
      at least one sequence V; and
   at least one additional circular sequence comprising
      at least one sequence IV being complementary with sequence IV',
      at least one sequence V, and
      at least one sequence VI encoding a biosensor sequence VI'.

7. The composition according to claim 1, wherein said analyte sequence I' or IV' is a sensor for at least one disease or disorder.

8. The composition according to claim 1, further comprising at least one polymerase enzyme.

9. The composition according to claim 1, further comprising a dNTP mixture.

10. The composition according to claim 1, further comprising at least one transducer substrate capable of providing a detectable signal from said biosensor sequence.

11. The composition according to claim 1, further comprising at least one transducer substrate capable of providing a detectable signal from said biosensor sequence wherein said transducer substrate is selected from the group consisting of a fluorescence inducing substrate, an optical inducing substrate, a electrochemical inducing substrate, a physicochemical inducing substrate, a piezoelectric inducing substrate and any combination thereof.

12. The composition according to claim 1, further comprising at least one transducer substrate capable of providing a detectable signal from said biosensor sequence wherein said signal is selected from the group consisting of a fluorescent signal, a physicochemical signal, an optical signal, a piezoelectric signal, a electrochemical signal and any combination thereof.

13. A method of detecting at least one analyte sequence I' comprising the steps of:
   contacting a sample with a composition comprising at least one hairpin sequence selected from the group consisting of SEQ. ID. NO. 4 and SEQ. ID. NO. 8; said at least one hairpin sequence comprising at least one analyte sequence I'; and at least one sequence II; and at least one circular sequence selected from the group consisting of SEQ. ID. NO. 2, SEQ. ID. NO. 6 and SEQ. ID. NO. 9; wherein said at least one circular sequence comprising: at least one sequence I being complementary with sequence I'; at least one sequence II; and at least one sequence III encoding a biosensor sequence III'; thereby forming a mixture of said sample and composition;
   detecting the biosensor sequence III' in said mixture; thereby detecting said sequence I'.

14. The method according to claim 13, wherein said detection is performed by contacting said mixture with a composition comprising at least one transducer substrate capable of providing a detectable signal from said biosensor sequence III'.

15. The method according to claim 13, wherein said detection is achieved for a concentration of 1*10-18M of said analyte sequence I' in said sample.

16. A method of detecting at least one analyte sequence I' and/or at least one analyte sequence IV' comprising the steps of:
   contacting a sample with a composition comprising at least one hairpin sequence comprising at least one analyte sequence I'; and at least one sequence II; at least one further hairpin sequence comprising: at least one analyte sequence IV'; and at least one sequence V; at least one circular sequence comprising: at least one sequence I being complementary with sequence I'; at least one sequence II; and at least one sequence III encoding a biosensor sequence III'; and at least one further circular sequence comprising: at least one sequence IV being complementary with sequence IV'; at least one sequence V; and at least one sequence VI encoding a biosensor sequence VI'; thereby forming a mixture of said sample and composition;
   detecting the biosensor sequence III' and/or biosensor sequence VI' in said mixture;
   thereby detecting said sequence I' and/or sequence IV',
   wherein each of the at least one hairpin sequence and the at least one further hairpin sequence is selected from the group consisting of SEQ. ID. NO. 4 and SEQ. ID. NO. 8, and
   wherein each of the at least one circular sequence and at least one further circular sequence is selected from the group consisting of SEQ. ID. NO. 2, SEQ. ID. NO. 6 and SEQ. ID. NO. 9.

17. The method according to claim 13 or 16, wherein said composition further comprises at least one polymerase enzyme and a dNTP mixture.

18. The method according to claim 13 or 16, wherein said composition further comprises at least one transducer substrate capable of providing a detectable signal from said biosensor sequence.

19. A kit comprising at least one component comprising the composition of claim 1 and at least one component comprising a composition comprising at least one transducer substrate capable of providing a detectable signal from said biosensor sequence; and instructions for use in the detection of an analyte sequence.

20. The kit according to claim 19, further comprising at least one transducer substrate capable of providing a detectable signal from said biosensor sequence.

* * * * *

```
                             SEQUENCE LISTING

<160> NUMBER OF SEQ ID NOS: 15

<210> SEQ ID NO 1
<211> LENGTH: 21
<212> TYPE: DNA
<213> ORGANISM: Artificial Sequence
<220> FEATURE:
<223> OTHER INFORMATION: Synthetic fragment

<400> SEQUENCE: 1
ttaggataga tatacgggtt c                                              21

<210> SEQ ID NO 2
<211> LENGTH: 84
<212> TYPE: DNA
<213> ORGANISM: Artificial Sequence
<220> FEATURE:
<223> OTHER INFORMATION: circular synthetic fragment

<400> SEQUENCE: 2
ggttaatcgc tgaatgacga acccgtatat ctatcctaac aggaattagt aaacaatgaa    60
gatgactgta catgggtgta acct                                          84

<210> SEQ ID NO 3
<211> LENGTH: 18
<212> TYPE: DNA
<213> ORGANISM: Artificial Sequence
<220> FEATURE:
<223> OTHER INFORMATION: modified synthetic fragment
<220> FEATURE:
<221> NAME/KEY: misc_feature
<222> LOCATION: (1)..(1)
<223> OTHER INFORMATION: modified with 6-Carboxyl-X-Rhodamine (ROX;
      fluorophore F1)
<220> FEATURE:
<221> NAME/KEY: misc_feature
<222> LOCATION: (18)..(18)
<223> OTHER INFORMATION: modified with Black Hole Quencher-2 (Q1)

<400> SEQUENCE: 3
tgactgttra ggaatgac                                                  18

<210> SEQ ID NO 4
<211> LENGTH: 56
<212> TYPE: DNA
<213> ORGANISM: Artificial Sequence
<220> FEATURE:
<223> OTHER INFORMATION: synthetic fragment

<400> SEQUENCE: 4
gaacccgtat atcaggaatt agtaaacaat gaagattagg atagatatac gggttc        56
```

```
<210> SEQ ID NO 5
<211> LENGTH: 21
<212> TYPE: DNA
<213> ORGANISM: Artificial Sequence
<220> FEATURE:
<223> OTHER INFORMATION: synthetic fragment

<400> SEQUENCE: 5
cccctctgag tcaggaaaca c                                              21

<210> SEQ ID NO 6
<211> LENGTH: 85
<212> TYPE: DNA
<213> ORGANISM: Artificial Sequence
<220> FEATURE:
<223> OTHER INFORMATION: circular synthetic fragment

<400> SEQUENCE: 6
ggttaatcgc tgagtactgt gtttcctgac tcagaggggc taattaccac tagacgatca    60
ttttaggata acatgggtgt aacct                                          85

<210> SEQ ID NO 7
<211> LENGTH: 18
<212> TYPE: DNA
<213> ORGANISM: Artificial Sequence
<220> FEATURE:
<223> OTHER INFORMATION: modified synthetic fragment
<220> FEATURE:
<221> NAME/KEY: misc_feature
<222> LOCATION: (1)..(1)
<223> OTHER INFORMATION: modified with 6-carboxylfluorescein (FAM;
      fluorophore F2)
<220> FEATURE:
<221> NAME/KEY: misc_feature
<222> LOCATION: (18)..(18)
<223> OTHER INFORMATION: modified with Black Hole Quencher-1 (Q2)

<400> SEQUENCE: 7
taggatatra ggagtact                                                  18

<210> SEQ ID NO 8
<211> LENGTH: 56
<212> TYPE: DNA
<213> ORGANISM: Artificial Sequence
<220> FEATURE:
<223> OTHER INFORMATION: synthetic fragment

<400> SEQUENCE: 8
gtgtttcctg actaattacc actagacgat catttcccct ctgagtcagg aaacac        56

<210> SEQ ID NO 9
<211> LENGTH: 61
<212> TYPE: DNA
<213> ORGANISM: Artificial Sequence
<220> FEATURE:
<223> OTHER INFORMATION: circular synthetic fragment

<400> SEQUENCE: 9
atctatccta acaggaatta gtaaacaatg aagacccaac ccgccctacc cgaacccgta    60
t                                                                    61

<210> SEQ ID NO 10
<211> LENGTH: 84
<212> TYPE: DNA
<213> ORGANISM: Artificial Sequence
<220> FEATURE:
<223> OTHER INFORMATION: synthetic fragment L2
```

<400> SEQUENCE: 10
ggttaatcgc tgaatgacga acccgtatat ctatcctaac aggaattagt aaacaatgaa    60
gatgactgta catgggtgta acct                                          84

<210> SEQ ID NO 11
<211> LENGTH: 22
<212> TYPE: DNA
<213> ORGANISM: Artificial Sequence
<220> FEATURE:
<223> OTHER INFORMATION: synthetic fragment Cap2

<400> SEQUENCE: 11
agcgattaac caggttacac cc                                            22

<210> SEQ ID NO 12
<211> LENGTH: 85
<212> TYPE: DNA
<213> ORGANISM: Artificial Sequence
<220> FEATURE:
<223> OTHER INFORMATION: synthetic fragment L6

<400> SEQUENCE: 12
ggttaatcgc tgagtactgt gtttcctgac tcagaggggc taattaccac tagacgatca    60
ttttaggata acatgggtgt aacct                                         85

<210> SEQ ID NO 13
<211> LENGTH: 22
<212> TYPE: DNA
<213> ORGANISM: Artificial Sequence
<220> FEATURE:
<223> OTHER INFORMATION: synthetic fragment Cap6

<400> SEQUENCE: 13
agcgattaac caggttacac cc                                            22

<210> SEQ ID NO 14
<211> LENGTH: 60
<212> TYPE: DNA
<213> ORGANISM: Artificial Sequence
<220> FEATURE:
<223> OTHER INFORMATION: synthetic fragment L9

<400> SEQUENCE: 14
atctatccta acaggaatta gtaaacaatg aagacccaac ccgccctacc cgaacccgta    60

<210> SEQ ID NO 15
<211> LENGTH: 21
<212> TYPE: DNA
<213> ORGANISM: Artificial Sequence
<220> FEATURE:
<223> OTHER INFORMATION: synthetic fragment Cap9

<400> SEQUENCE: 15
ttaggataga tatacgggtt c                                             21